United States Patent [19]

Fives-Taylor et al.

[11] Patent Number: 4,659,561

[45] Date of Patent: Apr. 21, 1987

[54] PROCESS FOR TREATING THE ORAL CAVITY

[75] Inventors: Paula Fives-Taylor; Charles P. Novotny, both of Burlington, Vt.

[73] Assignee: The University of Vermont and State Agricultural College, Burlington, Vt.

[21] Appl. No.: 714,948

[22] Filed: Mar. 22, 1985

Related U.S. Application Data

[63] Continuation-in-part of Ser. No. 467,800, Feb. 18, 1983, abandoned.

[51] Int. Cl.$^4$ .................. A61K 7/16; A61K 9/68; A61K 35/74; A61K 39/09
[52] U.S. Cl. ..................................... 424/48; 424/49; 424/50; 424/88; 424/92
[58] Field of Search ............................. 424/50, 92, 48

[56] References Cited

U.S. PATENT DOCUMENTS

| | | | |
|---|---|---|---|
| 4,324,782 | 4/1982 | Beck . | |
| 4,324,860 | 4/1982 | Hillman | 435/172 |
| 4,340,673 | 7/1982 | Stoudt et al. | 435/97 |
| 4,360,513 | 11/1982 | Buck | 424/56 |
| 4,360,514 | 11/1982 | Buck | 424/56 |
| 4,360,515 | 11/1982 | Buck | 424/56 |
| 4,362,713 | 12/1982 | Buck | 424/54 |
| 4,372,978 | 2/1983 | Gilbertson et al. | 424/343 |
| 4,374,122 | 2/1983 | Stroz et al. | 424/48 |
| 4,442,085 | 4/1984 | Colman et al. . | |

FOREIGN PATENT DOCUMENTS

| | | |
|---|---|---|
| 1375866 | 11/1974 | United Kingdom . |
| 1505513 | 3/1978 | United Kingdom . |
| 2033223 | 5/1980 | United Kingdom . |
| 2060647 | 5/1981 | United Kingdom . |
| 2143829A | 2/1985 | United Kingdom . |

OTHER PUBLICATIONS

Beachey, Edwin H., "Bacterial Adherence: Adhesin-Receptor Interactions Mediating the Attachment of Bacteria to Mucosal Surfaces," *Journal of Infectious Diseases*, vol. 143, No. 3, pp. 325-345 (1981).

Gibbons, R. J. et al., "Bacterial Adherence and the Formation of Dental Plaques," *Bacterial Adherence*, pp. 63-104 (1980).

Carlsson, J., "Dental Plaque as a Source of Salivary Streptococci," *Odontological Reviews*, vol. 18, pp. 173-178 (1967).

Carlsson, J., H. Grahnen, G. Jonsson and S. Wikner, 1970, *J. Dent. Res.*, 49(2): 415-418.

Clark, W. B., L. L. Bammann and R. J. Gibbons, 1978, *Infect. Immun.* 19: 846-853.

Clark, W. B., L. L. Bammann and R. J. Gibbons, 1978, *Infect. Immun.* 21: 681-684.

Elder, B., D. K. Boraker and P. M. Fives-Taylor, 1982, *J. Clin. Microbiol.* 16: 141-144.

Elder, B. and P. Fives-Taylor, 1983, *Abstr. of Annu. Meet. Am. Soc. Microbiol.* J5, p. 172.

Fachon-Kalweit, S. and P. Fives-Taylor, 1983, *Abstr. of Annu. Meet. Am. Soc. Microbiol.* J4 p. 172.

Fives-Taylor, P. 1982, In Schlessinger (ed.) *Microbiology-1982 Amer. Soc. Microbiol.* Washington, D.C., pp. 206-209.

Fives-Taylor, P. and S. Fachon, 1979, *Abstr. of 57th Gen. Sess. Int'l. Assoc. Dent. Res.* 436, p. 202.

Fives-Taylor, P., S. Fachon-Kalweit and J. Larson, 1981, *Abstr. 59th Gen. Sess. Int'l. Assoc. Dent. Res.* 1123, p. 590.

Fives-Taylor, P. and D. Thompson, 1985, "Surface Properties of Streptococcus sanguis FW 213 etc.", *Infect. Immun.* 47: pp. 752-759.

(List continued on next page.)

Primary Examiner—Shep K. Rose
Attorney, Agent, or Firm—Brumbaugh, Graves, Donohue & Raymond

[57] ABSTRACT

A process for treating the oral cavity to retard attachment of and the accumulation of microorganisms on surfaces of the teeth by blocking adherence of *Streptococcus sanguis* thereto. Fimbriae normally present on the surface of *S. sanguis*, fragments of the fimbriae or adherence factors including fimbrial antigen derived therefrom are used to block cell attachment by either competitive inhibition or to elicit an antibody response.

8 Claims, 4 Drawing Figures

OTHER PUBLICATIONS

Gibbons, Ronald J., "Bacteriology of Dental Caries," *Journal of Dental Research Supplement to No.* 6, vol. 43, pp. 1021–1028 (1964).

Gibbons, R. J., E. C. Moreno and D. M. Spinell, 1976, *Infect. Immun.* 14: 1109–1112.

Gibbons, R. J., et al., "Bacterial Adherence in Oral Microbial Ecology," *Annual Review of Microbiology*, pp. 19–44 (1975).

Gibbons, R. J. et al., "Concentration–Dependent Multiple Binding Sites on Saliva–Treated Hydroxyapatite for *Streptococcus sanguis*," *Infection and Immunity*, vol. 39, pp. 280–289 (1983).

Gibbons, R. J., et al., "Selective Adherence as a Determinant of the Host Tropisms of Certain Indigenous and Pathogenic Bacteria," *Infection and Immunity*, vol. 13, No. 1, pp. 238–246 (1976).

Gibbons, R. J., et al., "Selective Bacterial Adherence to Oral Epithelial Surfaces and Its Role as an Ecological Determinant," *Infect. Immun.*, vol. 3, pp. 567–573 (1971).

Gibbons, R. J., and J. van Houte, 1980, in E. H. Beachey (ed.), *Bacterial Adherence*, Chapman and Hall, N.Y.

Hay, D. I. 1967, *Arch. Oral Biol.* 12: 937–946.

Hillman, J. D., J. van Houte, and R. J. Gibbons, 1970, *Arch. Oral Biol.* 15: 899.

Lancy, P. Jr., B. Appelbaum, S. C. Holt and B. Rosan, 1980, *Infect. Immun.* 27: 663–670.

Orland, F., J. Blaney, R. Harrison, J. Reymeis, P. Trexier, M. Wagner, M. Gordon and T. Luckey, 1954 *J. Dent. Res.* 33: 147–174.

Socransky, S. S., A. D. Manganiello, D. Propas, V. Oron and J. van Houte, 1977, *J. Peridont. Res.*, 12: 90–106.

Thompson, D. W. and P. M. Fives–Taylor, 1983, *Abstr. of Annu. Meet. Am. Soc. Microbiol.* H24 p. 110.

Gibbons R. J., "Microbial Adhesion to Surface", *Soc. Chem. Industry*, Chapter 20, pp. 351–388 (1980), pp. 364, 370.

Gibbons, R. J., et al., "On the Formation of Dental Plaques", *Journal of Periodontology*, vol. 44, pp. 347–360 (1973).

Marx, J., "Vaccinating with Bacterial Pili", *Science*, vol. 209, pp. 1103–1106 (1980).

Kinetic analyses of attachment of S. mutans cells to saliva-coated hydroxyapatite (o) and to saliva-coated hydroxyapatite that contains bound S. sanguis cells (•).

Kinetic analyses of the attachment of S. sanguis cells to saliva-coated hydroxyapatite. (•) Normal cells with fimbriae; (o) Mutant cells lacking fimbriae; (X) normal cells whose fimbriae were coated with antibody.

PROCESS FOR TREATING THE ORAL CAVITY

The invention described herein was made in the course of, or under, a grant from the National Institute for Dental Research.

This application is a continuation-in-part of application Ser. No. 467,800, filed Feb. 18, 1983, now abandoned.

This invention relates to a process for treating the oral cavity of mammals to block or reduce the attachment of microorganisms to surfaces of the teeth therein. The invention also relates to compositions useful for this purpose and to methods for their preparation.

BACKGROUND OF THE INVENTION

The oral cavity of mammals develops a characteristic bacterial flora shortly after birth. The nature and number of the bacteria may vary in accordance with the host's general health and with outside influences such as diet. The bacterial species present in the oral cavity may also vary depending, inter alia, upon the location within the mouth and the maturity of the host. Bacteria accumulate in large quantities on tooth surfaces and this accumulation is called dental plaque. Mucosal surfaces, such as the buccal mucosa, the gingival crevice area and the tongue dorsum usually show much smaller numbers of bacterial cells, due at least partly to desquamation.

Dental plaque consists of mixed colonies of bacteria and may contain in excess of $10^8$ bacterial cells per mg. On uncleaned teeth, or areas that are protected, the plaque may reach a thickness of 300-500 cells. While the bacterial cells make up 60-70% by volume of the plaque, the balance is a matrix of bacterial and salivary polymers, together with portions of epithelial cells and leukocytes. At least 6 species of bacteria are found in plaque, and *Streptococcus sanguis* constitutes 10-50% of the organisms present.

The importance of dental plaque in initiating periodontal diseases and caries, as well as the yellowing of the teeth is well known. Dental caries is the destruction of the enamel, dentin, or cementum of teeth caused by bacterial action. It is generally believed that the process is one of direct demineralization, caused by accumulated lactic and other organic acids formed by bacteria in the dental plaque. Bacteria forming the group identified as *Streptococcus mutans* are most generally associated with the initial development of enamel lesions in humans. Other organisms associated with dental caries include the lactobacilli and some actinomyces.

Much of the work in the area designed to understand the mechanism of dental caries has been concentrated on organisms of the *S. mutans* group. The polymers formed as a result of the growth of *S. mutans* in high sucrose environment have been the subject of lengthy studies, and attempts have been made to form dental plaque in vitro using *S. mutans*.

The mechanism of dental plaque formation has been the subject of a number of careful studies. The surface of the enamel of teeth is a complex salt of calcium and phosphate called hydroxyapatite. Hydroxyapatite readily adsorbs glycoproteins. When normal teeth enamel surfaces are cleaned with abrasive down to the enamel surface and then exposed to normal fluids of the oral cavity, a thin film of adsorbed salivary components termed an "acquired pellicle" forms first on the surfaces. The pellicle is generally less than a micron in thickness and provides the receptor sites for the first microbial colonizers of the teeth. Its components include blood-group-reactive salivary mucins, and it is believed by some workers in the field that these serve as bacterial receptors.

Mechanical cleaning of teeth removes most of the accumulated dental plaque from those surfaces which are reached by the toothbrush or dental floss. Examination of the surfaces of a freshly cleaned tooth will show occasional small remnants of retained plaque which after an hour or two serve as points of accumulation for new dental plaque. At the same time, new colonies of plaque are formed on the surface of the pellicle as a result of attachment of single bacterial cells. The accumulation of bacterial cells continues over the course of time so that a continuous film of dental plaque is soon formed and unless removed from the tooth by abrasion or the action of saliva, the dental plaque, within two or three days, reaches its normal maximum thickness.

Dental plaque formation is now thought to involve two types of specific bacterial adherent interactions. Bacteria first attach, on a selective basis, to the acquired pellicle. In a second stage, bacteria accumulate by means of specific interactions with components of the existing plaque, including the plaque matrix and other bacterial cells. If adherence of the bacteria to the acquired pellicle could be prevented, subsequent colonization by a mixed flora of bacteria and the rate of formation of dental plaque could be substantially diminished. This is desirable to insure whiteness of the teeth as well as a means for reducing incidence of dental caries, gingivitis and periodontal disease.

Much of the substantial research in this field has been reviewed in the following articles:

Beachey, Edwin H., "Bacterial Adherence: Adhesin-Receptor Interactions Mediating the Attachment of Bacteria to Mucosal Surfaces", *Journal of Infectious Diseases*, Vol. 143, No. 3, pp. 325-345 (1981).

Gibbons, R. J. et al., "Bacterial Adherence And The Formation Of Dental Plaques", *Bacterial Adherence*, pp. 63-104 (1980).

Other references of interest include:

Carlsson, J., "Dental Plaque as a Source of Salivary Streptococci", *Odontological Reviews*, Vol. 18, pp. 173-178 (1967).

Carlsson, J., H. Grahnen, G. Jonsson and S. Wikner. 1970. *J. Dent. Res.* 49(2): 415-418.

Clark, W. B., L. L. Bammann and R. J. Gibbons. 1978. *Infect. Immun.* 19: 846-853.

Clark, W. B., L. L. Bammann and R. J. Gibbons. 1978. *Infect. Immun.* 21: 681-684.

Elder, B., D. K. Boraker and P. M. Fives-Taylor. 1982. *J. Clin. Microbiol.* 16: 141-144.

Elder, B. and P. Fives-Taylor. 1983. *Abstr. of Annu. Meet. Am. Soc. Microbiol.* J5. p. 172.

Fachon-Kalweit, S. and P. Fives-Taylor. 1983. *Abstr. of Annu. Meet. Am. Soc. Microbiol.* J4. p. 172.

Fives-Taylor, P. 1982. In Schlessinger (ed.) Microbiology-1982 *Amer. Soc. Microbiol.* Washington, D.C., pp. 206-209.

Fives-Taylor, P. and S. Fachon. 1979. *Abstr. of th Gen. Sess. Int'l Assoc. Dent. Res.* 436. p. 202.

Fives-Taylor, P., S. Fachon-Kalweit and J. Larson. 1981. *Abstr. 59th Gen. Sess. Int'l. Assoc. Dent. Res.* 1123.

Fives-Taylor, P. and D. Thompson, 1985, "Surface Properties of *Stretococcus Sanguis* FW 213 etc.", *Infect. Immun.* 47: pp. 752-759.

Gibbons, Ronald J., "Bacteriology of Dental Caries", *Journal of Dental Research Supplement to No.* 6, Vol. 43, pp. 1021–1028 (1964).

Gibbons, R. J., E. C. Moreno and D. M. Spinell. 1976. *Infect. Immun.* 14: 1109–1112.

Gibbons, R. J., et al., "Bacterial Adherence In Oral Microbial Ecology", *Annual Review of Microbiology*, pp. 19–44 (1975).

Gibbons, R. J., et al., "Concentration-Dependent Multiple Binding Sites on Saliva-Treated Hydroxyapatite for *Streptococcus sanguis*", *Infection and Immunity*, Vol. 39, pp. 280–289 (1983).

Gibbons, R. J., et al., "Selective Adherence as a Determinant of the Host Tropisms of Certain Indigenous and Pathogenic Bacteria", *Infection and Immunity*, Vol. 13, No. 1, pp. 238–246 (1976).

Gibbons, R. J., et al., "Selective Bacterial Adherence to Oral Epithelial Surfaces and Its Role as an Ecological Determinant", *Infect. Immun.*, Vol. 3, pp. 567–573 (1971).

Gibbons, R. J., and J. van Houte. 1980. In E. H. Beachey (ed.), *Bacterial Adherence*. Chapman and Hall, N.Y.

Hay, D. I. 1967. *Arch. Oral Biol.* 12: 937–946.

Hillman, J. D., J. van Houte and R. J. Gibbons. 1970. *Arch. Oral Biol.* 15: 899.

Lancy, P. Jr., B. Appelbaum, S. C. Holt and B. Rosan. 1980. *Infect. Immun.* 27: 663–670.

Orland, F., J. Blaney, R. Harrison, J. Reymeis, P. Trexier, M. Wagner, M. Gordon and T. Luckey. 1954. *J. Dent. Res.* 33: 147–174.

Socransky, S. S., A. D. Manganiello, D. Propas, V. Oron and J. van Houte. 1977. *J. Peridont. Res.*, 12: 90–106.

Thompson, D. W. and P. M. Fives-Taylor. 1983. *Abstr. of Annu. Meet. Am. Soc. Microbiol.* H24. p. 110.

STATEMENT OF THE INVENTION

It has now been found that bacteria known as *Streptococcus sanguis* are the first substantial colonizers of freshly cleaned teeth. Cells of *S. sanguis* attach first by binding to receptor sites on the acquired pellicle of a freshly cleaned tooth. After initial attachment of the *S. sanguis* cells, and their proliferation, a secondary colonization by *S. mutans* and other bacterial species takes place by attachment of cells thereof to receptor sites on *S. sanguis* cells in the initial colony of *S. sanguis*. By continuing to build in this manner, the dental plaque forms an environment conducive to the growth of the *S. mutans* and other microorganisms to the stage where they produce amounts of lactic acid and other organic acids sufficient to pierce the pellicle and demineralize the enamel surface.

It has been further found that by blocking the initial attachment of organisms of the *S. sanguis* group to the acquired pellicle, attachment of *S. mutans* and other dental caries producing organisms is inhibited or substantially retarded. Thus in accordance with the present invention, one method for blocking attachment of *S. sanguis* and of inhibiting the formation of dental plaque is provided wherein adherence factors, also called fimbrial antigen, obtained from the fimbriae of cells of the *S. sanguis* group are brought into contact with the tooth surface to combine with receptors thereon specific to *S. sanguis*. Since this process inhibits the formation of plaque, it also reduces dental discoloration, that is yellowing of the teeth, caused by a build-up of plaque.

This process can be accomplished by including the fimbrial antigens in suitable carriers such as a dentifrice, mouthwash, foodstuff, or beverage or otherwise bringing the substance into contact with the surface of the teeth at intervals sufficiently frequent to occupy receptor sites specific to *S. sanguis* and thereby reduce the binding of *S. sanguis* to receptor sites.

Further in accordance with the invention, initial attachment of organisms of the *S. sanguis* group to the acquired pellicle is inhibited or substantially retarded by administering to a mammalian host a vaccine specific to the fimbrial antigen obtained from the fimbriae of cells of *S. sanguis*. By administering the vaccine to the host, antibodies to the adherence factors are manufactured by the host. These antibodies appear thereafter in the saliva and there act to combine with the *S. sanguis* cells thereby neutralizing the cells' ability to attach at receptor sites specific to *S. sanguis* cells on the pellicle.

Still further in accordance with the invention, the cariogenicity of a foodstuff or beverage is inhibited or substantially reduced by incorporating adherence factors for *S. sanguis* into the foodstuff or beverage.

In addition, Applicants have discovered a fimbrial antigen from *Streptococcus sanguis*, characterized by being the only antigen obtained from surface material from adherent *S. sanguis* and detected in crossed immunoelectrophoresis against antibodies made against whole adherent *S. sanguis* cells that is (i) missing from surface material from nonadherent *S. sanguis* cells, and (ii) is capable of binding to antibodies made against *S. sanguis* fimbriae. Preferably, the antigen includes fimbriae from normal *S. sanguis* cells. In addition, it is preferred that the antigen is capable of binding to saliva-coated spheroidal hydroxyapatite and demonstrates intact fimbriae by electron microscopy. This fimbrial antigen is synonomous with the material described herein as "adherence factors".

Furthermore, the fimbrial antigen has been separated from other cell materials of *S. sanguis*, purified, and used as a vaccine to elicit antibodies. The resulting antibodies are characterized by being capable of binding to fimbriae of *S. sanguis*, by their inability to bind to nonfimbriated strains of *S. sanguis* and by their ability to immunoprecipitate *S. sanguis* cells having fimbriae, the cell-free fimbriae, or the fimbrial antigen.

DETAILED DESCRIPTION OF THE INVENTION

Figure 1:
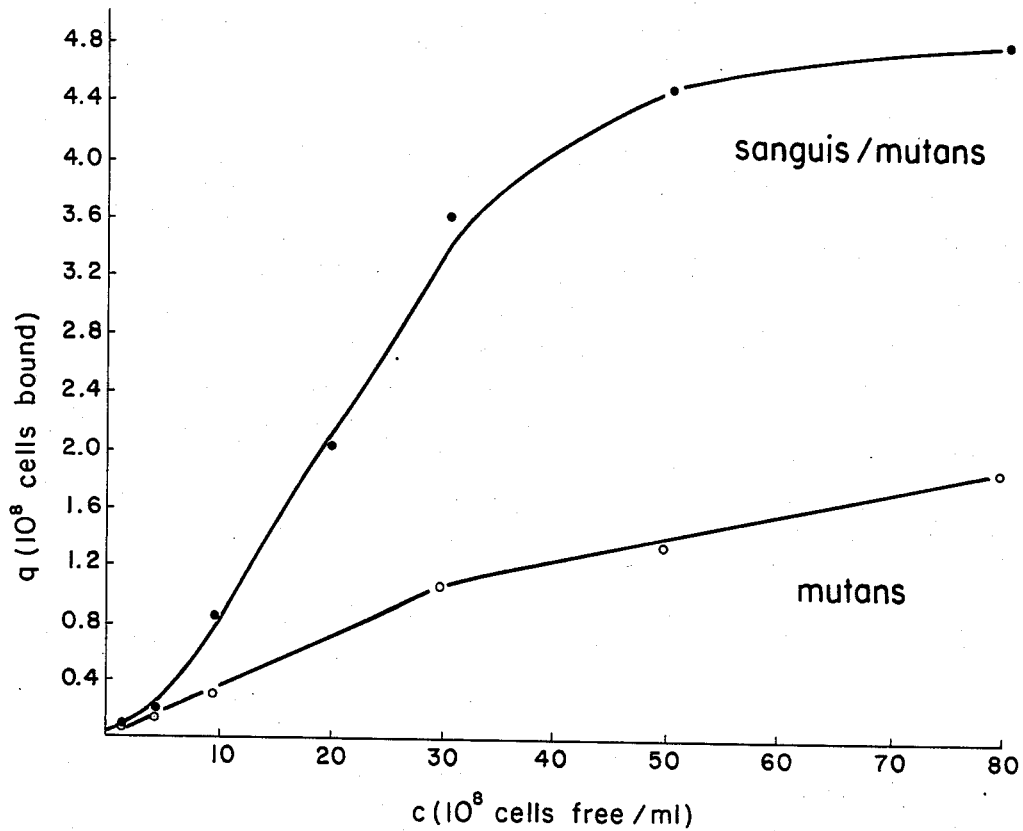
Figure 2:
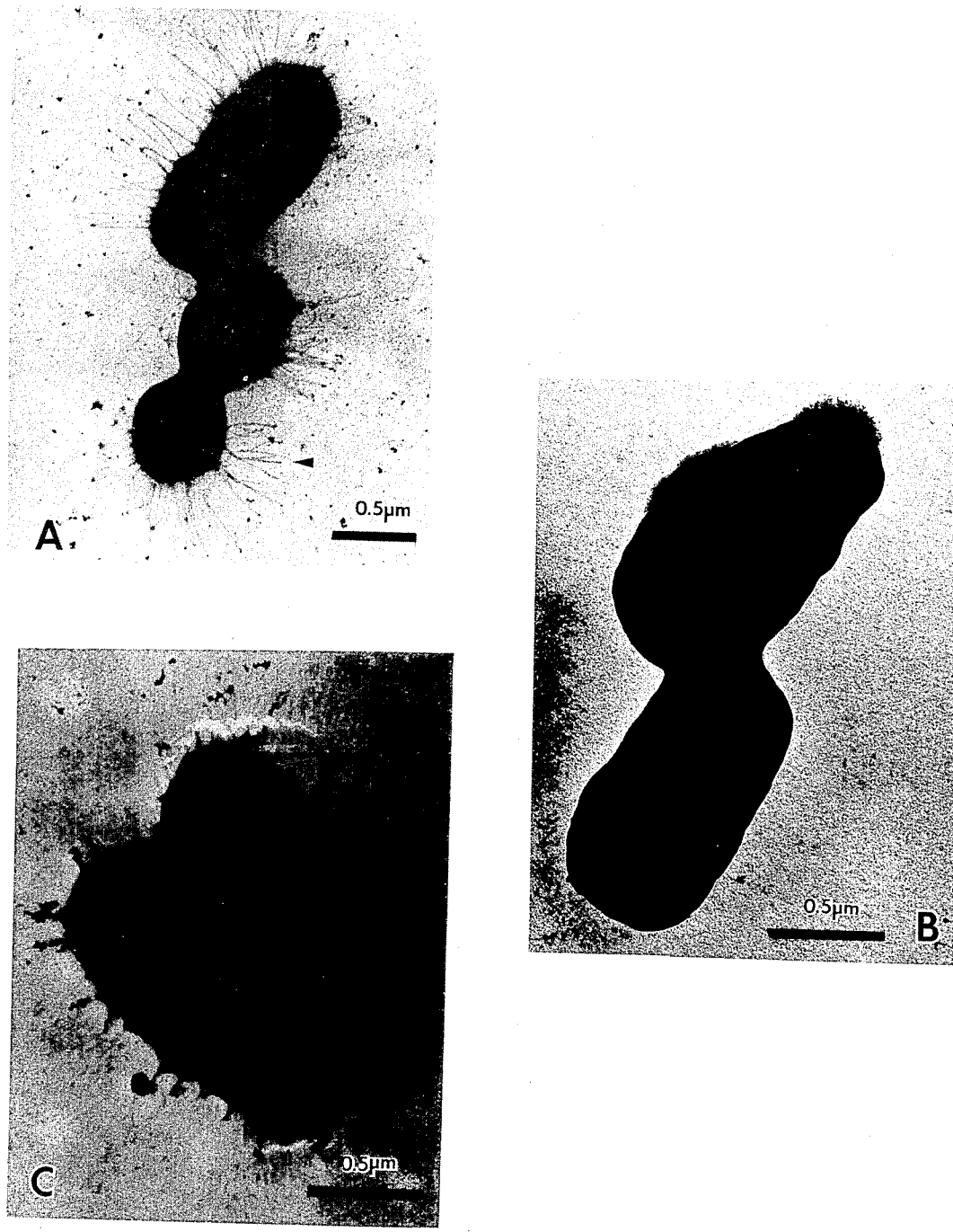
Figure 3:
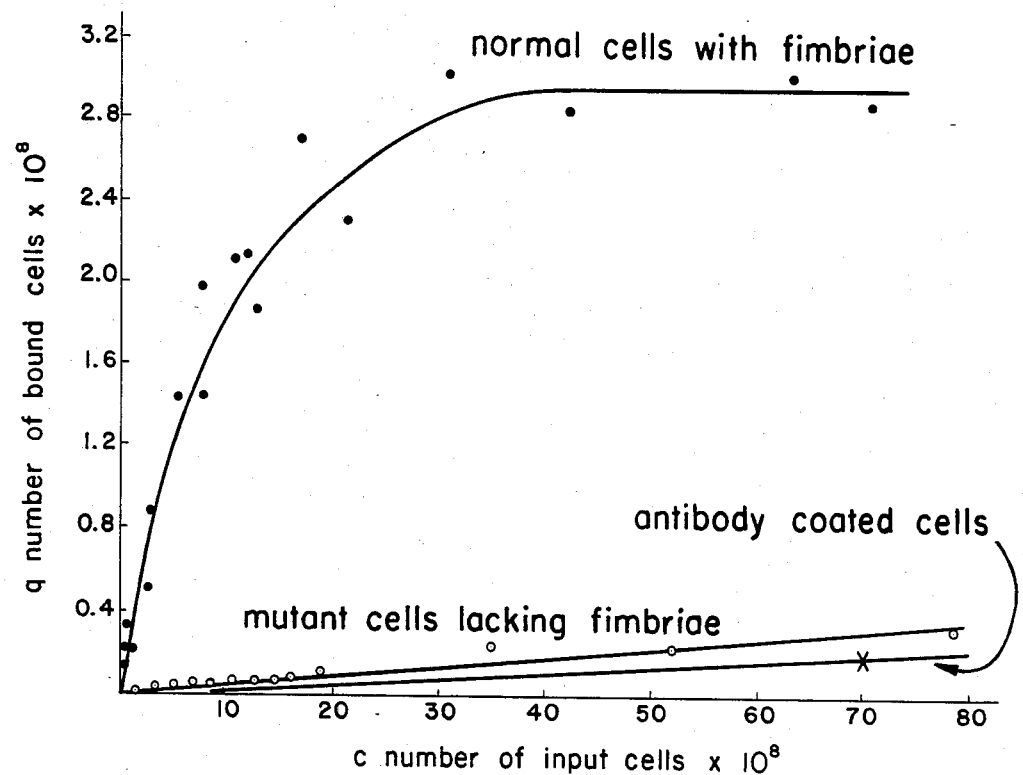
Figure 4:
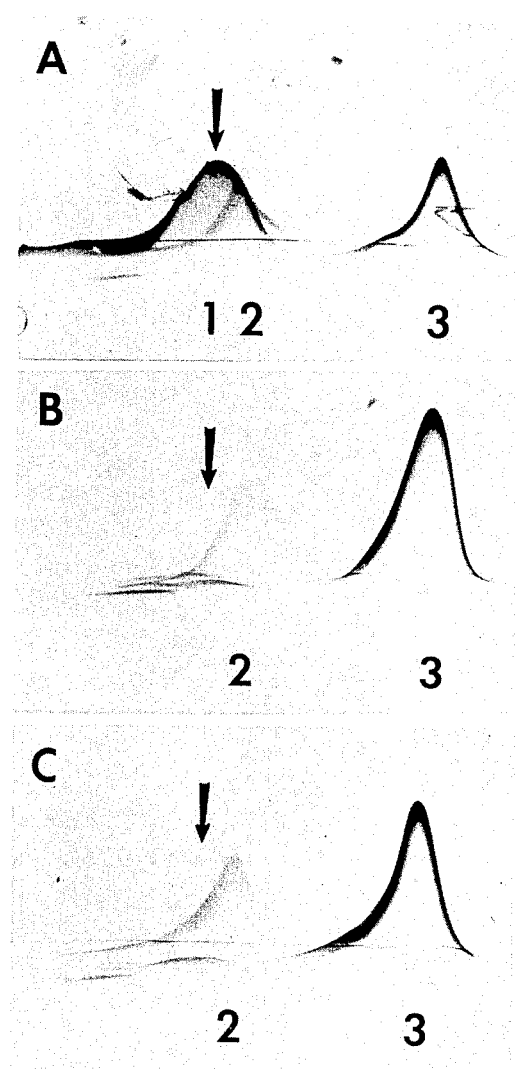

The invention will be further described with reference to the attached drawings, in which:

FIG. 1 is a graph showing that receptor sites for *S. mutans* are provided by *S. sanguis* on saliva-coated hydroxyapatite;

FIGS. 2A, B, and C are electron micrographs of *S. sanguis* cells negatively stained with phosphotungstic acid: A shows normal cells with fimbriae, shown with an arrow; B shows mutant cells lacking fimbriae; and C shows normal cells whose fimbriae are coated with antibody to fimbrial antigen;

FIG. 3 is a graph of data which demonstrates that fimbriated *S. sanguis* cells readily attach to saliva-coated spheroidal hydroxyapatite, while those without fimbriae and those whose fimbriae are coated with antibody do not; and FIGS. 4A, B and C show developed crossed immunoelectrophoretic gels of blended extracts from *S. sanguis* cells with fimbriae (A), blended extracts from *S. sanguis* mutant cells lacking fimbriae (B), and blended extracts of *S. sanguis* cells with fimbriae immunoprecipitated with monoclonal antibodies made to fimbriae (C), each run against whole polyclonal antisera made to intact normal cells.

The mechanism of dental plaque formation has been the subject of a number of careful studies. The surface enamel of teeth is a complex salt of calcium and phosphate called hydroxyapatite. Hydroxyapatite readily adsorbs glycoproteins. During the course of dental prophylaxis, the teeth are cleaned down to the enamel surface with abrasives. When teeth cleaned in this way are exposed to normal fluids of the oral cavity, a thin coating of adsorbed saliva, termed an "acquired pellicle", is formed first. This acquired pellicle provides the receptor sites for the first colonizers of the teeth. Hydroxyapatite beads suspended in saliva also acquire a pellicle, and are the industrial standard and experimental model for assaying bacterial adhesion (Gibbons and van Houte, 1980).

Saliva-coated spheroidal hydroxyapatite (SC-SHA) has been accepted as the industrial standard and experimental model for five major reasons: (1) Organisms with a high affinity for binding to teeth, have a high affinity for binding to SC-SHA; those with low affinity for binding to teeth, have a low affinity for binding to SC-SHA (Hillman et al., 1970); (2) Oral bacteria which specifically bind to the tongue or buccal epithelium, and do not bind to teeth, do not bind to SC-SHA either (Clark et al., 1978); (3) Among organisms that bind to teeth, the relative proportions of each species binding to teeth is similar to the proportion of those species that bind to SC-SHA (Gibbons and van Houte, 1980); (4) The selectivity of bacterial adsorption to SC-SHA parallels that observed in experiments performed directly in the mouths of humans (Clark et al., 1978); and (5) SC-SHA is recognized as possessing an additional advantage over in vivo experiments; radioactive materials can be used permitting the mechanism of adherence to be quantitated and described in physical chemical terms (Gibbons et al., 1976; Clark et al., 1978).

At least six species of bacteria are found in plaque and *S. sanguis* constitutes 10–50% of the organisms present. In addition to being the most numerous organism in plaque, *S. sanguis* also initiates plaque development. Studies of newly cleaned teeth and of newly erupted teeth of infants show that *S. sanguis* is the first organism to colonize these surfaces. The adherence of *S. sanguis* is followed by a succession of other microorganisms including *Streptococcus mutans*, *Actinomyces* sp. and various anaerobic bacteria. These bacteria use already formed *S. sanguis* plaque or the by-products of the plaque for their receptor sites. Applicants have found that *S. sanguis* binds first by binding to its receptor sites on the salivary pellicle and that then other microorganisms bind to the receptor sites provided on *S. sanguis*.

*S. mutans* attaches to the salivary pellicle only in low numbers and in a nonspecific manner. This is shown by reference to the kinetic analyses given in FIG. 1.

FIG. 1 shows Langmuir adsorption isotherms as kinetic analyses of attachment of *S. mutans* cells to saliva-coated hydroxyapatite, curve (o), and to saliva-coated hydroxyapatite that contains bound *S. sanguis* cells, curve (.). Data for these isotherms were obtained by the following procedure:

Broth grown log phase cells were labeled with $^3$H-thymidine in TH broth. Washed, labeled cells suspended in phosphate buffer (pH 6.0) were added at various concentrations to 40 mg of SC-SHA or 40 mg SC-SHA that had been preincubated for 1 hour with unlabeled *S. sanguis* FW213 cells. The cells and beads were incubated on an aliquot mixer at 37° C. for 1 hour. The beads and adsorbed cells were allowed to settle, the supernatant was removed, and the beads were washed 3 times in the buffer. The amount of radioactivity associated with the beads and supernatant was determined in a Beckman LS7500 Liquid Scintillation Counter and the counts converted to number of cells bound to 40 mg SC-SHA (q) and number of free cells (c). *S. mutans* cells alone, curve (o) display the relationship characteristic of nonspecific binding. *S. mutans* attachment to preformed *S. sanguis* plaque, curve (.), shows the curvilinear relationship characteristic of specific adherence. The shape of curve (o) implies that *S. mutans* does not have a receptor site on the salivary pellicle. *S. mutans* attaches to the salivary pellicle only in low numbers and in a non-specific manner. On the other hand, where the salivary pellicle is pretreated with *S. sanguis* by allowing *S. sanguis* to bind first and then *S. mutans* is added, two things happen, as shown by reference to curve (.). *S. mutans* binds in greater numbers and the binding is now specific, indicating that receptor sites for *S. mutans* are provided by *S. sanguis*.

Because *S. sanguis* is the first colonizer of cleaned teeth and because other bacteria attach to it, it is possible to reduce the formation of dental plaque on newly cleaned teeth by preventing the attachment of *S. sanguis* cells. Plaque development is reduced for two reasons: (1) *S. sanguis* itself is a major constituent of plaque and preventing it from attaching in itself reduces the mass of plaque, and (2) the ecological succession of microorganisms essential to the development of plaque is disrupted if adherence of a first colonizer, *S. sanguis*, to whom other species directly or indirectly bind, is blocked.

In studying the role of fimbriae in adherence of *S. sanguis*, Applicants have demonstrated that *S. sanguis* cells are covered with hairlike surface appendages called fimbriae. These are shown in the electron micrograph of FIG. 2A. Mutants that lack fimbriae were also isolated and representative cells thereof are shown in FIG. 2B. Antibodies that specifically bind to fimbriae were produced and were shown to coat fimbriae on normal cells. FIG. 2C is an electron micrograph showing cells whose fimbriae are coated with antibody.

Langmuir adsorption isotherms from kinetic analyses demonstrate that *S. sanguis* fimbriated cells readily attach to SC-SHA. FIG. 3 summarizes the results of these studies. The data was obtained by the following procedure:

Broth grown log phase cells were labeled with $^3$H-thymidine in TH broth. Washed, labeled cells suspended in phosphate buffer (pH 6.0) or cells preincubated with fimbrial antiserum were added at various concentrations to 40 mg of SC-SHA. The beads were incubated on an aliquot mixer at 37° C. for 1 hour. The beads and adsorbed cells were allowed to settle, the supernatant removed, and the beads then washed three times in the buffer. The amount of radioactivity associated with the beads and supernatant was determined in a Beckman LS7500 Liquid Scintillation Counter and the counts converted to number of cells bound to 40 mg SC-SHA (q) and number of input cells (c). Normal fimbriated cells of *S. sanguis* FW213, curve (.), display the curvilinear relationship characteristic of specific binding. The straight line shown by *S. sanguis* DT32EE, a nonfimbriated mutant, curve (o), suggests these cells bind nonspecifically and in very low numbers to SC- SHA Further, cells with fimbriae coated with antibody, curve (x) behave as mutant cells These data support that view that fimbriae perform an essential function in binding S. sanguis cells to the salivary pellicle The following additional observations by the inventors further support this idea First, among 140 clinical isolates collected from diverse sources by Dr. Fives-Taylor, only fimbriated cells adhere to SC-SHA. Second, among 20 mutants independently selected on the basis of their inability to adhere, 18 of the 20 lack fimbriae and the other two possess grossly abnormal fimbriae (Fives-Taylor and Thompson, 1983). Third, the extent of physical or chemical removal of fimbriae from otherwise normal cells correlates with the inability of these cells to bind to SC-SHA (Fives-Taylor et al., 1981). In addition, when surface material is prepared from S. sanguis cells by blending, three antigens can be detected in crossed immunoelectrophoresis against antibodies made against intact normal S. sanguis cells; see FIG. 4A. Antigen 2 and 3 can be found on similar preparations of nonadherent mutants, but antigen 1 is missing in preparations from nonadherent cells; see FIG. 4B. Also, treatment of surface material prepared from normal fimbriated S. sanguis cells with antibodies made specifically to fimbriae removes antigen 1 from these preparations; see FIG. 4C. These data demonstrate that antigen 1, hereafter fimbrial antigen, is the antigen involved in adherence. The fimbrial antigen may contain fimbriae, as demonstrated by electron microscopy. Furthermore, the fimbrial antigen produces the same high molecular weight pattern in SDS gel electrophoresis as purified fimbriae. A detailed description of FIGS. 4A, 4B and 4C. and the methods used in their preparation is given below in Example 7. These data are convincing evidence that S. sanguis fimbriae, or a component thereof, are responsible for the adherence of S. sanguis to the salivary pellicle.

In summary, the active factor found by applicants and used in accordance with the present invention is a fimbrial antigen from *Streptococcus sanguis*, characterized by being the only antigen obtained from surface material from adherent S. sanguis and detected in crossed immunoelectrophoresis against antibodies made against whole adherent S. sanguis cells that is (i) missing from surface material from nonadherent S. sanguis cells, and (ii) is capable of binding to antibodies made against S. sanguis fimbriae. The antigen may include fimbriae from normal S. sanguis cells. In addition, it is preferred that the antigen is capable of binding to saliva-coated spheroidal hydroxyapatite and that it demonstrate intact fimbriae by electron microscopy. This fimbrial antigen is the active factor in the materials described herein and in our parent application as adherence factors and sometimes as fimbriae.

It is recognized that S. mutans colonizes teeth in a localized and persistent manner. S. mutans has been detected consistently in high proportions on some surfaces but not on others even within the same mouth. It has been speculated that the inability of S. mutans to spread to said other tooth surfaces is because of its relatively feeble ability to attach to teeth and to the low numbers of this organism generally found in saliva. Applicants believe that S. mutans colonizes the surface of teeth by attaching to other bacterial cells. Specifically, applicants believe that numerous receptors on the acquired pellicle are specific for S. sanguis. The S. sanguis in turn provides receptor sites, permitting the attachment of S. mutans. Thus if the adhesion of S. sanguis to the teeth can be prevented, either by blocking the specific receptors on the teeth with fimbrial antigen or by neutralizing the adherence factors of S. sanguis cells by binding thereof with antibodies, then the bacterial colonization of the teeth will be minimized. In the absence of S. sanguis on the pellicle, there are substantially fewer sites for attachment by S. mutans, and as a consequence, the build-up of dental plaque is retarded, the yellowing of the teeth is minimized and the incidence of dental caries is diminished.

In summary, adherence of S. sanguis to the tooth enamel may be blocked by two separate mechanisms. First, the adherence may be blocked by presenting to the receptor on the tooth surface an adherence factor, the fimbrial antigen, obtained from S. sanguis. As an alternative procedure, the mammalian host may receive a vaccine comprising the fimbrial antigen obtained from S. sanguis. The vaccine raises an antibody response to the antigen. The antibodies are present in the saliva, where they combine with the antigen on the surface of S. sanguis and neutralize the antigen thereby preventing the combination of S. sanguis with receptors on the tooth surface. As a further alternative, preparations containing the antibodies can be introduced into the mouth. In either event, the S. sanguis found in the saliva or contributed by desquamation are swallowed and very few become attached to the teeth or other surfaces of the mouth.

The invention is further illustrated by the following examples:

EXAMPLE 1

The fimbriae, adherence factors or fimbrial antigen from S. sanguis cells used according to this invention are prepared by the following procedure:

S. sanguis cells are grown to confluency on $8\frac{1}{2} \times 12\frac{1}{2} \times 2$ inch plates containing trypticase soy agar (Difco). The growth is aseptically scraped from the plates after 24 hours and the cells are collected into centrifuge bottles. The collected cells are washed with phosphate buffered saline at pH 7.0 and recollected by centrifugation. The fimbriae are removed from the washed cells by resuspending the cells in 3.0 M potassium iodide (KI) and blending in a Sorvali Omnimixer for 20 minutes at 16,000 rpm. The blending serves to shear the fimbriae from the cells by mechanical dislodgement.

The whole cells are separated from the fimbriae by centrifugation at 10,000 rpm for 15 minutes. the supernate containing tPhe fimbriae is dialyzed against water to remove the KI. As the KI is removed, the fimbriae or adherence factors form aggregated bundles.

40 μg of the crude preparation of aggregated S. sanguis fimbriae are contacted with 25.2 cm$^2$ surfaces of saliva-coated hydroxyapatite (the in vitro model for adhesion to teeth—see Gibbons et al. 1976) to block the receptor sites for S. sanguis adhesion. When $1 \times 10^9$ S. sanguis cells are then presented to the surfaces of saliva-coated hydroxyapatite the adhesion of the cells is inhibited by about 90%.

In individuals who are colonized with S. sanguis cells, approximately $1 \times 10^6$ cells of the organism can be found per ml of saliva (Carlsson, 1967). Therefore, it is estimated that a single tooth of 2–3 cm$^2$ would be exposed to $3 \times 10^6$ S. sanguis cells per cm$^2$ of its surface (Gibbons et al. 1983). A whole mouth with a tooth surface area of 90 cm$^2$ would be exposed to approximately $1 \times 10^8$ S. sanguis cells. Accordingly, it is calculated that a maximum of 2.0 mg of *S. sanguis* fimbriae will prevent the adhesion of 90% of the *S. sanguis* cells onto the surface of the teeth.

Partial purification of the adherence factors or fimbrial antigen is accomplished by resuspending the aggregated bundles in 3.0 M KI, dialyzing the collected factors against water, and harvesting the soluble fraction.

The adherence factors are further purified by suspending the partially purified factors or antigen, in 3.0 M KI for centrifugation. The KI continuous density gradients are formed in 10×½ centimeter polyethylene tubes by centrifuging in a SW 55 Ti rotor at 35,000 rpm at 4° C. for 60 hours. A discrete band, corresponding to a KI density of 1.42 g/ml, is visible in each tube containing adherence factors. This band, containing the adherence factors or antigen, is collected by puncturing the bottom of each tube and collecting drops. Once the band is collected, it is dialyzed against 1.0 M KI. The adherence factors or antigen can be frozen and stored for at least 6 months.

EXAMPLE 2

A mouthwash within the scope of the invention is prepared by mixing the following ingredients in the proportions indicated in 200 milliliters of water:

|  | Grams |
|---|---|
| cetylpyridinium chloride | 0.45 |
| domiphen bromide | 0.05 |
| SD alcohol 38 F | 185.0 |
| glycerin polysorbate 80 | 20.0 |
| flavorants and colorants | 0.05 |

The aqueous solution of purified adherence factors or antigen, which is prepared in accordance with Example 1, is dialyzed a 40° C. for two days against several changes of water to remove the 1.0 M KI. The recovered adherence factors or antigen are lyophilized for 8 hours to remove the water. 50 mg of the adherence factors or fimbrial antigen are added to the above solution.

Water is added to the above ingredients in an amount sufficient to bring the total volume of the composition to 500 milliliters. The composition has a pH of about 7.2.

One ounce of the mouthwash is utilized for 20 seconds in the morning and after meals to prevent the formation of dental plaque, whiten the teeth and retard the incidence of caries formation.

EXAMPLE 3

A toothpaste within the scope of the invention is prepared as described below:

|  | Grams |
|---|---|
| carboxymethylcellulose | 8.6 |
| glycerine/propylene glycol | 100.0 |
| water | 200.0 |
| methyl para-hydroxy-benzoate | 132.0 |
| saccharin solution (50%) | 1.0 |
| oil of spearmint | 2.0 |
| non-ionic surface active agent | 25.0 |
| mineral oil | 9.0 |
| dicalcium phosphate | 510.0 |
| adherence factors or | 0.05 |

| | Grams |
|---|---|
| fimbrial antigen | |

The glycerine and propylene glycol are mixed together, and about one fifth of this solution is added to the carboxymethylcellulose and mixed to form a slurry. The methyl para-hydroxy-benzoate is diluted with 20 grams of water and then added to the slurry and mixed well to form a gel. The remainder of the glycerine-propylene glycol solution is thoroughly incorporated into the gel. The saccharin solution, oil of spearmint, mineral oil and the non-ionic surface active agent are added to the gel and thoroughly mixed. The lyophilized, purified adherence factors or antigen, prepared and purified in accordance with Example 1 and lyophilized in accordance with Example 2, are added to the gel and thoroughly mixed. The powdered dicalcium phosphate is incorporated with mixing into the gel in small amounts until it has all been added. Water is added as needed to the above ingredients to facilitate mixing. The above mixture is then milled to form a smooth, white toothpaste.

The toothpaste is utilized in regular daily brushing to prevent the formation of dental plaque, whiten the teeth and retard the incidence of caries formation, gingivitis, and peridontal disease.

EXAMPLE 4

A chewing gum is prepared having the following composition:

|  | Grams |
|---|---|
| sodium saccharin | 0.05 |
| mannitol | 26.00 |
| gum base | 30.00 |
| sorbitol | 42.95 |
| adherence factors (fimbrial antigen) | 0.05 |

The gum base is heated until it is of syrupy consistence and washed with 3 to 4 percent aqueous hydrochloric acid, dilute aqueous sodium bicarbonate solution and water in turn. The sorbitol, mannitol and sodium saccharin are mixed with the gum base and the mixture is cooled to 23° C. The lyophilized, purified adherence factors or antigen, prepared and purified in accordance with Example 1 and lyophilized in accordance with Example 2, are blended into the mixture. The entire mass is mixed well, allowed to cool to 15° C. and formed into 1 gram units of desired shape.

EXAMPLE 5

A vaccine within the scope of the invention is prepared by the following procedure:

Ten Sprague Dawley rats are pre-bled from the heart to obtain about 2 ml of blood from each rat to serve as the controls. The teeth of the ten rats are mechanically cleaned to remove all traces of plaque.

A 0.02 percent solution of purified adherence factors or antigen, prepared according to Example 1, is dialyzed against water to remove the 1.0 M KI. 1.0 mg of the factors are emulsified with 2.5 ml of Freunds complete adjuvent until the mixture thickens to the point where it is difficult to draw up in a needle. Five rats are each inoculated with 0.5 ml of the emulsion of adherence factors and Freunds complete adjuvent at 4 sites on each rat. The other five rats are inoculated with 0.5 ml of Freunds complete adjuvent at 4 sites on each rat. All injections are subcutaneous. A booster inoculation of 1.0 mg per rat is given 21 days after the primary inoculation. Adjuvent is not used in the booster.

The antibodies against adherence factors are found in the blood of the five rats inoculated with the adherence factors while antibodies against adherence factors are not found in the control blood samples. The rats inoculated with the purified adherence factors show whiter teeth than the control rats and considerably less plaque is removed from the teeth of immunized rats than controls.

EXAMPLE 6

Fimbrial antigen prepared according to the procedure set forth in Example 1 was used to block the attachment of S. sanguis cells to SC-SHA. Removal of fimbriae from the cell surface by mechanical means provides intact cells which will not attach to SC-SHA, as well as a source of free fimbriae. The addition of fimbrial antigen to suspensions of normal cells having fimbriae blocked the attachment of S. sanguis cells, as shown in Table 1 below:

TABLE 1
BLOCKING OF S. SANGUIS ADHERENCE TO SC-SHA BY FIMBRIAE ANTIGEN

| SAMPLE | DILUTION | CELLS BOUND × $10^7$ | % ADHESION |
|---|---|---|---|
| FIMBRIAL ANTIGEN | ½ | 2.0 | 22 |
| CONTROL | " | 9.0 | 100 |
| FIMBRIAL ANTIGEN | 1/5 | 2.4 | 26 |
| CONTROL | " | 9.0 | 100 |
| FIMBRIAL ANTIGEN | 1/10 | 3.9 | 43 |
| CONTROL | " | 9.0 | 100 |

Furthermore, the fraction containing the fimbrial antigen described as Antigen 1 in Example 7 below, blocks adhesion by approximately 90%, as shown in Table 2:

TABLE 2
BLOCKING OF S. SANGUIS ADHERENCE TO SC-SHA BY FRACTION CONTAINING ANTIGEN 1 (FIG. 4A)

| SAMPLE | CELLS BOUND × $10^7$ | % ADHESION |
|---|---|---|
| ANTIGEN 1 | 0.27 | 10 |
| CONTROL | 2.64 | 100 |

Material from the 1.42 g/ml band prepared according to Example 1 blocks adhesion of S. sanguis to SC-SHA and reacts with monoclonal and polyclonal antibodies made to fimbriae. The material contains high molecular weight complexes and a protein of ca. 38,000 d molecular weight as identified with monoclonal antibodies in western blots; see Example 7.

EXAMPLE 7

This example describes a method for the preparation of the fimbrial antigen of the present invention and the characterization thereof. Also described are the method used for preparing antibodies to the fimbrial antigen as well as the antibody preparations themselves. Procedures and materials used in preparing the data used to prepare and characterize the antigen and antibodies and used to develop the data given in the drawings are also given.

Antibodies raised against a fimbriated, adhesive strain of S. sanguis were found to block the adhesion of this organism to saliva-coated hydroxyapatite. Antibodies were made specific for adhesion antigens by (1) adsorptions with isogenic, nonadhesive mutants (for rabbit polyclonal antibody, e.g. adsorbed antibody), or (2) selection based on nonreactivity with two nonadhesive mutants (for monoclonal antibody). Rabbit antibody raised against isogenic, nonfimbriated nonadhesive mutants served as a control for antibodies present, but not related to fimbriation. Adsorbed antibody and monoclonal antibody were shown to be specific for fimbriae (antigen 1, FIG. 4A) as both antibodies (1) could be seen by immune electron microscopy to bind to 3.6 nm fimbriae, (2) reacted only with the fimbriated parent and not the mutants in a bactELISA assay, and (3) could immunoprecipitate fimbriae from fimbrial extracts of S. sanguis. Antibodies isolated from preimmune and mutant sera did not react with fimbriae in any of the above assays. Adsorbed antibody and monoclonal antibody were capable of blocking the adhesion of S. sanguis cells to saliva-coated hydroxyapatite. Adsorbed antibody, purified to IgG, was an effective inhibitor of adhesion without causing interfering cellular aggregation. Monoclonal antibody, cleaved to Fab fragments to prohibit cell to cell crosslinking, was also a potent inhibitor of S. sanguis cell adhesion to SC-SHA; see Table 5. Both IgG from mutant sera and normal mouse Fab fragments could not be shown to block adhesion.

The following study, using both polyclonal and monoclonal antisera, determined that fimbriae and fimbrial antigen are involved in the adhesion of S. sanguis to SC-SHA, and establishes methods for blocking such adhesion.

The following abbreviations are used in this example: Saliva-coated, spheroidal hydroxyapatite (SC-SHA); Phosphate buffered saline, 0.05M, pH 7.4 (PBS); Polyclonal immunoglobulins (PAb); Adsorbed immunoglobulins (AdAb); Monoclonal immunoglobulins (MAb); Immunoglobulin G (IgG); Papain cleaved IgG (FAb); and Sodium dodecyl sulfate-polyacrylamide gel electrophoresis (SDS-PAGE).

In addition, the following bacterial strains were used: Streptococcus sanguis FW213 (Obtained from Roger Cole, National Institutes of Health, Bethesda, Md.) was the primary organism used. In addition, isogenic mutants of S. sanguis FW213, nonadhesive to SC-SHA, and identified as VT507 and VT321 were isolated in applicant's laboratory. All strains were kept frozen at −70° C., and portions were removed weekly for use.

Growth conditions.

S. sanguis cells were inoculated from a weekly stock plate onto a plate containing tryptose blood agar base with 5% defibrinated sheep's blood, and incubated for 12–15 h at 36° C. in 5% $CO_2$. The cells were harvested into TH broth to a concentration of approximately $1.5 \times 10^8$ cells per ml, incubated aerobically at 36° C. with gentle agitation, and assayed turbidimetrically until an optical density equivalent to $5.5 \times 10^8$ bacteria per ml was reached. The cells were washed 3 times by centrifugation at 12,000×g for 15 min at 4° C. with 0.05M phosphate buffered saline (PBS) pH 7.4. S. sanguis cells for adsorption experiments were grown on 33×23 cm plates containing trypticase soy agar for 12–13 h at 36° C. in 5% $CO_2$. The cells were harvested and washed 3 times by centrifugation.

Polyclonal antibody production.

Rabbits were injected subcutaneously with $1\times10^9$ live *S. sanguis* cells in sterile saline. After 1-2 months, the rabbits were boosted intravenously 3 times per week with live bacteria for a period of 2 weeks. The inoculum size for boosting was increased from $1\times10^8$ cells to $1\times10^9$ cells over the two week period. The animals were then bled by cardiac puncture and the sera were harvested.

Adsorption of rabbit polyclonal antisera.

Polyclonal antisera were enriched for immunoglobulins by ammonium sulfate precipitation as described below under antibody purification. The immunoglobulin fraction from the polyclonal antisera (PAb) was enriched for adhesion antibody by adsorbing the PAb 8 times with approximately 0.4g wet weight of cells from a nonadhesive mutant at 36° C. with the 4th and 8th adsorption at 4° C. The mutant cells and PAb were rocked for 30 min, then centrifuged at $12,000\times g$ for 15 min and the pellet discarded. The adsorbed supernatant (AdAb) was used directly or further purified to IgG.

Monoclonal antibody production and selection.

The production of monoclonal antibody F51 (MAb) was based on techniques developed by Kohler, G., and C. Milstein, 1975, "Continuous cultures of fused cells secreting antibody of predefined specificity", *Nature*, 256: 495-497, and modified by Gefter, M. L., D. H. Margulies, and M. D. Scharff, 1977, "A simple method for polyethylene glycol-promoted hybridization of mouse myeloma cells". *Somat. Cell Genet.*, 3: 231-236. Briefly, mice were immunized on day 0, 35 and 140 with live *S. sanguis* cells. The spleen cells were removed and fused with myeloma line x63Ag8.653, (Kearney et al., 1979 *J. Immuno l.* 123: 1548-1550), using polyethyleneglycol 1000. The resulting hybridoma colonies were screened in a bactELISA assay for antibody reactive with *S. sanguis* FW213, and nonreactive with 2 isogenic nonadhesive mutants (VT321, VT507). These cells were cloned by limiting dilution on a rat thymocyte feeder layer, retested for antibody reactivity, then expanded and injected into pristane-primed mice for ascites development. Ascites fluid containing normal mouse immunoglobulins was obtained by injecting pristane-primed mice with the parental myeloma line x63Ag8.653.

Antibody purification.

Polyclonal antisera were partially purified by serial ammonium sulfate precipitation at 40, and 33% saturation, each time reserving the pellet, followed by dialysis against PBS. Protein concentration was determined using the Bio-Rad protein assay based on the method of Bradford, *Anal. Biochem.* 72: 248-254, using bovine gamma globulin as a standard. The immunoglobulin fraction (PAb) was further purified by ion exchange chromotography on a DE52 column equilibrated with 0.0175M phosphate buffer, pH 7.0. The breakthrough fraction was collected and found to contain IgG by both 12.5% SDS-PAGE, Laemmli, 1970, *Nature* 227: 680 685 and immunoelectrophoresis against goat anti-rabbit IgG, Grabar et al. 1953, *Biochem. Biophys. Acta* 190: 193-194. Antibody-containing ascites fluid was partially purified by ammonium sulfate precipitation at 45% saturation. Monoclonal antibody F51 (MAb) was cold precipitable, and was further purified by cycles of cold precipitation in PBS. Nonimmune ascites fluid was dialyzed into 0.02M Tris HCl, pH 8.0, and further purified by ion-exchange chromatography with DE52 using a KCl gradient of 0-0.2M KCl. The IgG containing peak was confirmed by its reaction with rabbit antimouse IgG in an Ouchterlony diffusion assay, *Acta Pathol. Microbiol. Scand.* 26: 507-515. Protein concentrations of purified IgG's were calculated by UV absorbance at 280 nm using an extinction coefficient of 14.3.

Fab production.

Fab fragments were prepared from purified IgG by digestions with papain, as originally described by Porter, 1959, *Biochem. J.* 73: 119-127. A final concentration of 2% papain was added to a solution of 5 to 10mg of IgG in 0.2M cysteine. The mixture was incubated for 2 h at 37° C. Proteolysis was ended and sulfhydryl groups alkylated by raising the pH to 8-9 with 1M Tris base, followed by the addition of iodoacetamide (final concentration, 0.025M) and a 15 min incubation at 37° C. Extent of cleavage was monitored by 12.5% SDS-PAGE.

BactELISA.

The bactELISA assay used was that described in Elder, B. L., D. K. Boraker, and P. Fives-Taylor, 1982, "Whole-bacterial cell enzyme-linked immunosorbent assay for *Streptococcus sanguis* fimbrial antigens", *J. Clin. Microbiol.*, 16: 141-144.

Immune Electron Microscopy.

*S. sanguis* cells grown and washed as described above, were resuspended to $5.4\times10^8$ bacteria per ml in PBS. Immunoglobulin fractions of AdAb's, MAb's and nonimmune antibodies were diluted in PBS, and mixed with 1 ml of the *S. sanguis* cell suspension. The bacteria-antibody mixture was incubated for 60 min at 4° C. then centrifuged at $12,000\times g$ for 15 min. The pellet was thoroughly drained, then resuspended in 0.1 ml of PBS. One drop of the antibody-coated bacteria was mixed with a drop of 3% phosphotungstic acid, and applied to a formvar coated copper specimen grid. After 1 min, the excess fluid was blotted away the grid was dried and examined in a Phillips 300 electron microscope at 60KV. Calibration was performed with a waffled carbon grating replica.

Ferritin-labeled Immune Electron Microscopy.

*S. sanguis* cells were treated as described above. However, after antibody coating, the bacteria were washed three times with PBS to remove nonbound antibody. A ferritin-conjugated goat anti-mouse IgG (H+L) was diluted 1:100 in PBS, and the bacteria were resuspended in 1 ml of this diluted conjugate. After 30 min incubation at room temperature, the bacteria were washed three times in PBS, then stained and examined as before.

Preparation of Antigen Extracts.

Streptococcal surface antigens were prepared by a modification of the method of Example 1. Briefly, surface antigens from *S. sanguis* FW213 (adhesive, fimbriated parent) and *S. sanguis* VT321 (an isogenic, nonadhesive, nonfimbriated mutant) are removed by high speed pulse blending in a Sorvall omnimixer (16,000 rpm, $20\times1$ min, 4° C.) in 3M potassium iodide. Potassium iodide, a chaotropic agent, was used to prevent the hydrophobic fimbriae from pelleting with the cells. Cells were removed by centrifugation at $12,000\times g$ for 15 min and the bacterial wet weight was determined. The supernatant fluid containing the fimbriae was dialyzed to remove potassium iodide and concentrated by lyophilization. In order to maintain in the extracts the relative proportion of antigens found in the parent and mutants, the lyophilized material was resuspended in sterile, distilled water to a concentration equivalent to 3 g wet weight of cells per ml. Nonsoluble material was removed by a 3 min spin in a Micro-centrifuge, Model 235B (Fisher Scientific, Pittsburgh, Pa.). Further purification of the fimbrial antigen was accomplished by isopycnic centrifugation in 3.5M potassium iodide for 16 h at 58,000 rpm in a Beckman L2-65B ultracentrifuge fitted with a Type 65 fixed-angle rotor (Beckman, Palo Alto, Calif.). Only the visible band from FW213 at a buoyant density of 1.42 g per ml contained free fimbriae and was reactive with both AdAb and MAb.

Immunoelectrophoresis of Antigen Extracts.

Antigens present in cell extracts were separated electrophoretically by crossed immunoelectrophoresis, (Clarke, M. H. G., and T. Freeman, 1968, "Quantitative immunoelectrophoresis of human serum proteins", Clin. Sci., 35: 403–413) in 12 ml of 1% agarose, (tris-barbiturate buffer, pH 8.6, ionic strength 0.02), poured onto an 8.4×9.4 cm glass plate. Five $\mu$l of antigen extract were placed into a well and electrophoresed for 1.5 h at 10 V per cm on a cooled (4° C.) LKB Multiphor apparatus (LKB Products, Bromma, Sweden). The gel was trimmed to isolate the agarose strip containing the antigens, and transferred to a 7×8.4 cm Gelbond film. For the second dimension of electrophoresis, 150 $\mu$l of PAb were added to 6 ml of molten 1% agarose (cooled to 50° C.), and poured onto the remaining area of the Gelbond film forming a connection with the agarose strip containing the separated antigens. Electrophoresis was performed at 2 V per cm for 16–25 h. To prepare the gel for staining, it was pressed twice for 3 min with several layers of filter paper and paper towels under a flat weight, then washed for at least 45 min in several changes of 0.1M NaCl. The gel was pressed once more, then dried at 50° C. Staining was done for 5 min in 1% Coomassie blue in 45% ethanol-10% glacial acetic acid. Destaining was done in the same solution, without Coomassie blue.

Immunoprecipitation of antigen.

(i) Blended extracts. 10 $\mu$l of MAb, AdAb, or PBS were added to 5 $\mu$l of blended FW213 extract incubated at 37° C. for 15 min, and loaded onto a crossed immunoelectrophoresis gel for separation and identification. Only unbound antigen is able to move through the 1% agarose gel.

(ii) Gradient fractions. Five $\mu$l of MAb were added to 2 $\mu$l of the dialyzed 1.42 g per ml band obtained from isopycnic centrifugation of blended extracts of S. sanguis FW213 and VT321. These preparations were viewed by phase microscopy at 800×. Material without antibody and antibody alone served as controls.

Adhesion of S. sanguis to saliva-coated, spheroidal hydroxyapatite (SC-SHA).

(i) Clarification of saliva. To minimize batch to batch variability of adhesion factors in saliva, large pools (ca. 3.0 liters) of paraffin stimulated saliva from over 200 volunteers were collected on ice. The saliva was clarified by centrifugation at 17,000×g for 10 min at 4° C. The supernatant fluid was heated to 60° C. for 30 min to inactivate enzymes that destroy the adhesion factors (Gibbons, R. J., and D. M. Spinnel, 1970, "Salivary induced aggregation of plaque bacteria", p. 207–215. In W. D. McHugh (ed.), Dental Plaque, E. and S. Livingston, Inc., Edinburgh). Sodium azide was added to a final concentration of 0.05% and the clarified saliva was frozen in 10 ml portions at −30° C.

(ii) Hydroxyapatite. Spheroidal Hydroxyapatite Beads (SHA), BDH Chemicals Ltd., Poole, England, were suspended in 0.067 M phosphate buffer (pH 6.0) (PB) and settled for 5 min. The supernatant fluid containing the "fines" was aspirated. This washing was repeated 4 times. The remaining SHA beads were resuspended in phosphate buffer and captured on a 12 $\mu$m polycarbonate membrane filter. The beads were allowed to dry and were distributed in 40 mg portions.

(iii) Preparation of SC-SHA. One milliliter of pooled clarified saliva was added to tubes containing 40 mg SHA and incubated with rocking sufficient to keep the beads in suspension for 1 h at 37° C. A saliva coating corresponding to a salivary pellicle was formed. The beads were allowed to settle and the supernatant fluid was removed and discarded. The beads were washed 3 times in phosphate buffer.

(iv) Adhesion assay. The adhesion assay used was a modification of that developed by Gibbons, R. J., E. C. Moreno, and D. M. Spinell, 1976, "Model delineating the effects of a salivary pellicle on the adsorption of Streptococcus miteor onto hydroxyapatite", Infect. Immun., 14: 1109–1112. Broth grown log phase FW213 cells were labeled in TH broth (Todd Hewitt, tryptose blood agar base) with 2.0 $\mu$Ci per ml [$^3$H]-thymidine. Labeled cells were centrifuged and washed 3 times with phosphate buffer. Cell suspensions, ranging from $5\times10^8$ x cells per ml to $5\times10^9$ cells per ml, were made in phosphate buffer and sonicated for 15 s at 95 W in a Bronson sonifier with an ultrasonic cuphorn. A 100 $\mu$l sample was removed from the $1\times10^9$ cells per ml concentration to determine the specific activity of the cells. One milliliter of each cell concentration was added to duplicate tubes of SC-SHA and incubated 1h at 37° C. with gentle rocking. The beads were allowed to settle and 200 $\mu$l of the supernatant fluids were removed to determine the free cell concentration. The beads were then washed 3 times in buffer and transferred to scintillation vials to determine the number of cells bound to SC-SHA. All samples were counted in a Beckman scintillation counter (Model LS 7500). The number of bound cells was plotted against the number of free cells.

(v) Adhesion blocking assay. The effects of various antibody preparations on the adhesion of S. sanguis FW213 to the SC-SHA was done using the adhesion protocol described above with an additional step. After the S. sanguis cells were labeled with [$^3$H]-thymidine and washed, they were resuspended in phosphate buffer (PB), or PB plus antibody and rocked for 1 h at 37° C. The cells were washed 2 times in PB, resuspended, and then added to the SC-SHA for the adhesion phase of the assay. The extent of blocking was calculated by comparing the number of antibody-coated cells that bound to SC-SHA with the number of buffer-coated cells.

Characterization of antibody.

(i) Adsorbed antibody. Extensive adsorption of FW213 PAb with either mutant decreased the bactELISA reactivity of the sera for the mutant from control levels to that seen for preimmune serum (Table 3). These sera continued to show reactivity against the parent strain although at a slightly diminished level. Serum adsorbed with one mutant had the same decreased reactivity against the second mutant as it did with itself. Sera raised against either nonadhesive mutant reacted equally well with the parent. These sera served as controls for antibody present but not related to adhesion.

TABLE 3
Characterization of Ammonium Sulfate Precipitated Polyclonal Antiserum by BactELISA

| | Antibody activity[a] in a bactELISA with *Streptococcus sanguis:* | | |
|---|---|---|---|
| Antibody Specificity | Control (FW213) | Non-adherent mutant (VT321) | Non-adherent mutant (VT507) |
| Preimmune | >256.0 | >256.0 | >256.0 |
| Control (FW213) | 0.5 | 1.0 | 1.0 |
| Fimbrial (FW213/VT321[b]) (AdAb) | 2.0 | >256.0 | >256.0 |
| Fimbrial (FW213/VT507[b]) (AdAb) | 16.0 | >256.0 | >256.0 |
| Non-adherent mutant (VT321) | 1.0 | 0.5 | 1.0 |
| Non-adherent mutant (VT507) | 2.0 | 4.0 | 2.0 |

[a]Activity is expressed as the protein concentration μg/ml required to give an optical density of 0.5 in the bactELISA.
[b]Antibody was raised against the parent strain and adsorbed with the mutant.

(ii) Monoclonal antibody. The monoclonal antibody secreting line used was F51. Line F51 was chosen for further analysis based on its high titer in ascites fluid (ELISA activity still detectable at a $1^{-6}$ dilution), and on its ability to agglutinate or precipitate its corresponding antigen in various assay systems. Monoclonal antibody F51 (MabF51) was found to be IgG3 by Ouchterlony diffusion against class and subclass specific antibodies. In the bactELISA, MAb reacted specifically with the adhesive parent strain, FW213, and was nonreactive with the two isogenic, nonadhesive mutants. The Fab fragments of MAb maintained high titer, specific reactivity towards *S. sanguis* FW213 in the bactELISA. As seen in Table 4, the MAb Fab fragments were strongly reactive at 3 μg per ml against *S. sanguis* FW213, while even concentrations >300 μg per ml failed to show reactivity against strain VT321. SDS-PAGE of these fragments revealed no uncleaved IgG. The fragments were also tested for their functional ability to agglutinate *S. sanguis* FW213 cells. Uncleaved MAb was a potent agglutinator of these cells. Following papain cleavage, the MAb was unable to agglutinate the FW213 cells at any concentrations between 0.3 and 300 μg per ml.

TABLE 4
Characterization of Monoclonal Fab Fragments by BactELISA

| | Fab Activity[a] in a bactELISA with *Streptococcus sanguis:* | |
|---|---|---|
| Fab Source | Control (FW213) | Non-adherent mutant (VT321) |
| Normal Mouse IgG | >60 | >60 |
| Monoclonal IgG | 3 | >300 |

[a]Activity is expressed as the protein concentration (μg/ml) required to give an optical density of 0.3 in the bactELISA.

Immune electron microscopy.

AdAb was seen to coat fimbriae on intact *S. sanguis* FW213 and fimbriae free in suspension. The antibody coated fimbriae, both attached and free from the cell exhibited a constant width of 3.6 nm (2 SD =0.9nm). Neither preimmune or mutant strain directed antibodies were able to label fimbriae. The MAb was seen to coat the peritrichous fimbriae of *S. sanguis* FW213, using ferritin labeled immune electron microscopy but reacted with no structures on the mutants. Normal mouse immunoglobulins were used as a control to demonstrate that the ferritin conjugate did not nonspecifically bind to fimbriae.

Immunoelectrophoresis of antigen extracts.

Immunoelectrophoretic analyses of *S. sanguis* FW213 blended extracts revealed that there were three distinct antigens recognized by the PAb made in response to the whole cell (FIG. 4A). For convenience, these antigens were labeled Ag 1, Ag 2, and Ag 3 in the order they migrated from the origin. Similar analyses of the nonadhesive, nonfimbriated mutant, VT321, revealed that there were only two distinct antigens recognized by PAb (FIG. 4B). These data clearly demonstrate that there is only one antigenic difference between the parent strain and its isogenic mutant and that difference is Ag 1. As VT321 resulted from a single mutation, and the only observable difference in VT321 is a loss of fimbriae (9), these data imply that Ag 1 is fimbrial antigen. Similar analysis of nonfimbriated VT507 also demonstrated a loss of Ag 1. In addition, immunoprecipitation of the FW213 blended extracts with AdAb or MAb resulted in the loss of only Ag 1 from the antigen profile (FIG. 4C).

Immunoprecipitation of fimbriae.

To demonstrate further that the MAb is specific for fimbriae, the MAb was used to immunoprecipitate free fimbriae that banded at a density of 1.42 g per ml in isopynic centrifugation. When fimbriae were immunoprecipitated they formed large, visible aggregates. When viewed by phase microscopy at 800 ×, these aggregates appeared as refractile large mats. Electron microscopy of these mats revealed the 3.6 nm fimbriae previously demonstrated with AdAb. The corresponding antibody treated VT321 fraction and the uncentrifuged VT321 extract, as well as the FW213 fraction without antibody and the antibody alone, showed no aggregates when viewed by phase microscopy. Analyses with AdAb gave similar results.

Adhesion blocking ability of antibody.

(i) Adsorbed antibody. Purified IgG from *S. sanguis* FW213 AdAb was capable of blocking the adhesion of FW213 to SC-SHA. At an IgG concentration of 100 μg per ml adhesion was inhibited by greater than 90% (Table 5). Mutant VT507 directed IgG, with a bactELISA titer slightly higher than that of the AdAb, was unable to block adhesion at a concentration of 400 μg per ml. Antibody directed against *S. sanguis* FW213 formed small agglutinates (less than 10 cells in size) during incubation in the adhesion assay. Significantly, IgG directed against the nonadhesive mutants formed agglutinates equivalent in size (or larger) to those seen with AdAb IgG, yet adhesion was not blocked.

TABLE 5
Adhesion Blocking Ability of Adsorbed Purified Polyclonal IgG

| | Percent Adhesion to SC-SHA IgG concentration (μg/ml)[a]: | | | | |
|---|---|---|---|---|---|
| IgG Source | 400 | 100 | 50 | 12 | 0 |
| Preimmune | 92 | 89 | 95 | 83 | 100 |
| Fimbrial (FW213/VT507[b]) (AdAb) | 8 | 6 | 32 | 117 | 100 |
| Non-adherent mutant (VT507) | 100 | | | | |

[a]Protein concentration was determined by optical density at 280 nm and an extinction coefficient of 14.3.
[b]Antibody was raised against the parent strain and adsorbed with the mutant.

(ii) Monoclonal antibody. MAb cleaved to Fab fragments, was found to be a potent and specific inhibitor of *S. sanguis* FW213 adhesion to SC-SHA. When these fragments, at concentrations from 40–250 μg per ml were added to *S. sanguis* FW213, the adhesion of these cells was reduced 86–98% compared to untreated cells (Table 4). When normal mouse immunoglobulins, also cleaved to Fab fragments, were used in place of MAb adhesion was decreased by only 0-16%, indicating that the blocking was specific for the MAb.

TABLE 6

Adhesion Blocking Ability of Monoclonal Fab Fragments

| Fab Source | Percent Adhesion to SC-SHA Fab digest concentration (μg/ml)[a]: | | | |
| --- | --- | --- | --- | --- |
| | 250 | 80 | 40 | 0 |
| Normal Mouse IgG | 84 | 118 | 143 | 100 |
| Monoclonal IgG | 2 | 5 | 14 | 100 |

[a]Protein concentration was determined by optical density at 280 nm.

The antibodies used in this study were raised against the adhesive parent, and made specific for adhesion antigens by (1) adsorptions with isogenic, nonadhesive mutants (for AdAb) or (2) selection based on nonreactivity with the nonadhesive mutants (for MAb). The nonadhesive mutants had originally been selected solely for their inability to adhere to SC-SHA. This approach favored the identification of any surface structures involved in the adhesion of *S. sanguis* FW213 to the salivary pellicle; this is important since several groups of researchers have proposed that *S. sanguis* adhesion involves multiple types of bonds with differing affinities. However, the analyses of these mutants indicated that only the fimbrial antigen of *S. sanguis* plays an important role in the adhesion of this organism to SC-SHA.

This study was undertaken to locate and identify additional antigens or surface structures involved in the adhesion of *S. sanguis* FW213 to SC-SHA. Crossed immunoelectrophoretic analyses demonstrated three major antigens associated with *S. sanguis* FW213 blended extracts. Similar analyses of the isogenic nonadhesive mutants used in this study revealed a single antigenic difference from the parent; a lack of Ag 1. As partially purified fimbriae, when examined by crossed immunoelectrophoresis, migrate in the same manner as Ag 1 in blended extracts, these data suggest that Ag 1 and fimbriae are the same. Hence, no additional antigens were found involved in the adherence of *S. sanguis* to the salivary pellicle.

Both the AdAb and MAb used in this study were found to be specific for fimbriae. The evidence was four fold: (1) Both AdAb and MAb could be seen by immune electron microscopy to bind to the 3.6 nm fimbriae on intact cells and free in suspension. These antibodies did not recognize any structures on the mutants; (2) Both AdAb and MAb reacted with the fimbriated parent but not the mutants in a bactELISA assay; (3) Both AdAb and MAb were observed by phase microscopy to precipitate the fimbriae from partially purified fimbrial extracts of FW213. These antibodies did not immunoprecipitate any material from mutant extracts prepared in the same manner; and (4) When blended extracts of FW213 were immunoprecipitated with AdAb or MAb and analyzed by drossed immunoelectrophoresis, only Ag 1 was missing.

The specificity of these antibodies is demonstrated by: (1) the binding of these antibodies to attached and free fimbriae, (2) their inability to react with nonadherent and nonfimbriated mutants, (3) their ability to immunoprecipitate fimbriated cells, free fimbriae and antigen 1 but not nonfimbriated cells, or antigens 2 and 3. A vaccine consisting of these fimbriae elicits an antibody response directed against the adhesion factors of *S. sanguis* and these antibodies bind to the fimbriae on cells and thus prevents *S. sanguis* from adhering to teeth thereby reducing plaque development.

The fimbrial preparations that have been used above are nontoxic either in topical applications or when injected as antigen. *S. sanguis* cells occur naturally in the mouth and this material is swallowed without ill effects. Although *S. mutans* does cross-react with human heart tissue, no evidence, published or unpublished, is known that *S. sanguis* cross-reacts with any human tissue. Furthermore, no antigens are known in common to *S. sanguis* and *S. mutans*. Nevertheless, for caution, vaccine preparations should contain only those antigens that specifically elicit an immunological response necessary to obtain dental prophylaxis.

We claim:

1. In the art of utilizing toothpaste and mouthwash dentifrice and chewing gum daily in the morning and after meals to prevent formation of dental plaque, whiten the teeth and retard incidence of dential caries formation, the improvement which comprises the step of utilizing topically for 20 seconds in the morning and after means, (a) one ounce of mouthwash containing 50 milligrams per 500 milliliters, or (b) a toothpaste containing 0.05 grams per kilogram, or (c) a chewing gum containing 0.05 g./100 g., of lyophilized fimbrial antigen from *Streptococcus sangius,* the antigen characterized by being the only antigen obtained from surface material from adherent *S. sanguis* and detected in crossed immunoelectrophoresis against antibodies made against whole adherent *S. sanguis* cells that is (i) missing from surface material from non-adherent *S. sanguis* cells, and (ii) is capable of binding to antibodies made against *S. sanguis* fimbriae.

2. In the art of utilizing toothpaste and mouthwash dentifrice and chewing gum daily in the morning and after meals to prevent formation of dental plaque, whiten the teeth and retard incindence of dental caries formation, the improvement which comprises the step of utilizing topically for 20 second in the morning and after meals, (a) one ounce of mouthwash containing 50 milligrams per 500 milliliters, or (b) a toothpaste containing 0.05 grams per kilogram, or (c) a chewing gum containing 0.05 g./100 g., of lyophilized fimbrial antigen from *Streptococcus sangius* comprising fimbriae from normal *S. sangius* cells, and the antigen being further characterized by being the only antigen obtained from surface material from adherent *S. sanguis* and detected in crossed immunoelectrophoresis against antibodies made against whole adherent *S. sangius* cells that is (i) missing from surface material from non-adherent *S. sangius* cells, and (ii) is capable of binding to antibodies made against *S. sangius* fimbriae.

3. In the art of utilizing toothpaste and mouthwash dentifrice and chewing gum daily in the morning and after meals to prevent formation of dental plaque, whiten the teeth and retard incidence of dental caries formation, the improvement which comprises the step of utilizing topically for 20 seconds in the morning and after meals, (a) one ounce of mouthwash containing 50 milligrams per 500 milliliters, or (b) a toothpaste containing 0.05 grams per kilogram, or (c) a chewing gum containing 0.05 g./100 g., of lyophilized fimbrial antigen from *Streptococcus sangius* comprising fimbriae from normal *S. sangius* cells, and the antigen being further characterized by:
  (a) being capable of binding to saliva-coated spheroidal hydroxyapatite, and
  (b) being the only one of three antigens obtained from surface material from adherent *S. sangius* and detected in crossed immunoelectrophoresis against antibodies made against whole adherent *S. sangius* cells that is
  (i) missing from surface material from non-adherent *S. sangius* cells,
  (ii) demonstrates intact fimbriae by electron microscopy, and
  (iii) binds to antibodies made against *S. sangius* fimbriae.

4. In a process for preventing the formation of dental plaque in mammals, the step of blocking adherence of *S. sangius* cells to tooth surfaces of the oral cavity, wherein the blocking step is carried out by flushing the oral cavity with a preparation containing adherence factors in an effective amount of fimbrial antigen from *S. sangius*.

5. In a process for preventing the formation of dental plaque in mammals, the step of blocking adherence of *S. sangius* cells to tooth surfaces of the oral cavity, wherein the blocking step is carried out by contacting teeth with a dentrifice containing an effective amount of fimbrial antigen from *S. sanguis*.

6. In a process for preventing the formation of dental plaque in mammals, the step of blocking adherence of *S. sanguis* cells to tooth surfaces of the oral cavity by exposing the surface to fimbrial antigen from *Streptococcus sangius*, the antigen characterized by being the only antigen obtained from surface material from adherent *S. sangius* and detected in crossed immunoelectrophoresis against antibodies made against whole adherent *S. sangius* cells that is
  (i) missing from surface material from non-adherent *S. sangius cells*, and
  (ii) is capable of binding to antibodies made against *S. sangius* fimbriae,
  substantially free of viable *S. sangius* cells, to hereby block adherence of *S. sangius* cells to tooth surfaces of the oral cavity.

7. In a process for retarding the yellowing of teeth in mammals, the step of blocking adherence of *S. sangius* cells to tooth surfaces of the oral cavity by exposing the surfaces to fimbrial antigen from *Streptococcus sangius*, the antigen characterized by being the only antigen obtained from surface material from adherent *S. sangius* and detected in crossed immunoelectrophoresis against antibodies made against whole adherent *S. sangius* cells that is
  (i) missing from surface material from non-adherent *S. sangius* cells, and
  (ii) is capable of binding to antibodies made against *S. sangius* fimbriae,
  substantially free of viable *S. sangius* cells, to hereby block adherence of *S. sangius* cells to tooth surfaces of the oral cavity.

8. In a process for retarding the yellowing of teeth in humans, the step of blocking adherence of *S. sangius* cells to tooth surfaces of the oral cavity by exposing the surfaces to fimbrial antigen from *Streptococcus sangius*, the antigen characterized by being the only antigen obtained from surface material from adherent *S. sangius* and detected in crossed immunoelectrophoresis against antibodies made against whole adherent *S. sangius* cells that is
  (i) missing from surface material from non-adherent *S. sangius cells*, and
  (ii) is capable of binding to antibodies made against *S. sangius* fimbriae,
  substantially free of viable *S. sangius* cells, to thereby block adherence of *S. sangius* cells to tooth surfaces of the oral cavity.

* * * * *

UNITED STATES PATENT AND TRADEMARK OFFICE
CERTIFICATE OF CORRECTION

PATENT NO. :    4,659,561
DATED      :    April 21, 1987
INVENTOR(S):    Paula Fives-Taylor et al.

It is certified that error appears in the above-identified patent and that said Letters Patent is hereby corrected as shown below:

Col. 2, line 62, "th" should read --57th--;

Col. 2, line 65, after "1123" insert --p. 590.--;

Col. 2, line 67, "Stretococcus" should read --Streptococcus--;

Col. 6, line 11, after "(o)" insert a comma;

Col. 8, line 44, "Sorvali" should read --Sorvall--;

Col. 8, line 50, "tPhe" should read --the--;

Col. 9, line 39, "a" should be --at--;

Col. 9, line 39, "40° C." should read --4° C.--;

Col. 13, line 48, before "40" insert --50,--;

Signed and Sealed this

First Day of December, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,659,561

DATED : April 21, 1987

INVENTOR(S) : Paula Fives-Taylor et al.

It is certified that error appears in the above-identified patent and that said Letters Patent is hereby corrected as shown below:

Col. 13, line 59, "680 685" should read --680-685--;

Col. 16, line 26, after "$10^8$" delete "x";

Col. 17, line 23, "$1^{-6}$" should read --$10^{-6}$--;

Col. 19, line 59, "drossed" should read --crossed--;

Col. 20, line 21, "dential" should read --dental--;

Col. 20, line 28, "sangius" should be --sanguis--;

Col. 20, line 40, "incindence" should read --incidence--;

Col. 20, line 47, "sangius" should be --sanguis--;

Col. 20, line 48, "sangius" should be --sanguis--;

Col. 20, line 50, "sangius" should be --sanguis--;

Col. 20, line 52, "sangius" should be --sanguis--;

Col. 20, line 55, "sangius" should be --sanguis--;

UNITED STATES PATENT AND TRADEMARK OFFICE
CERTIFICATE OF CORRECTION

PATENT NO. : 4,659,561
DATED : April 21, 1987
INVENTOR(S) : Paula Fives-Taylor et al.

It is certified that error appears in the above-identified patent and that said Letters Patent is hereby corrected as shown below:

Col. 20, line 57, "sangius" should be --sanguis--;

Col. 20, line 68, "sangius" should be --sanguis--;

Col. 21, line 1, "sangius" should be --sanguis--;

Col. 21, line 6, "sangius" should be --sanguis--;

Col. 21, line 8, "sangius" should be --sanguis--;

Col. 21, line 12, "sangius" should be --sanguis--;

Col. 21, line 15, "sangius" should be --sanguis--;

Col. 21, line 20, "sangius" should be --sanguis--;

Col. 21, line 24, "sangius" should be --sanguis--;

Col. 21, line 27, "sangius" should be --sanguis--;

Col. 21, line 36, "sangius" should be --sanguis--;

Col. 21, line 38, "sangius" should be --sanguis--;

UNITED STATES PATENT AND TRADEMARK OFFICE
CERTIFICATE OF CORRECTION

PATENT NO. : 4,659,561
DATED : April 21, 1987
INVENTOR(S) : Paula Fives-Taylor et al.

It is certified that error appears in the above-identified patent and that said Letters Patent is hereby corrected as shown below:

Col. 21, lines 39-40, "sangius" should be --sanguis--;

Col. 22, line 2, "sangius" should be --sanguis--;

Col. 22, line 4, "sangius" should be --sanguis--;

Col. 22, line 5, "sangius" should be --sanguis--;

Col. 22, line 6, "sangius" should be --sanguis--;

Col. 22, line 9, "sangius" should be --sanguis--;

Col. 22, line 11, "sangius" should be --sanguis--;

Col. 22. line 13, "sangius" should be --sanguis--;

Col. 22, line 15, "sangius" should be --sanguis--;

Col. 22, line 18, "sangius" should be --sanguis--;

UNITED STATES PATENT AND TRADEMARK OFFICE
CERTIFICATE OF CORRECTION

PATENT NO. : 4,659,561
DATED : April 21, 1987
INVENTOR(S) : Paula Fives-Taylor et al.

It is certified that error appears in the above-identified patent and that said Letters Patent is hereby corrected as shown below:

Col. 22, line 20, "sangius" should be --sanguis--;

Col. 22, line 21, "sangius" should be --sanguis--;

Col. 22, line 22, "sangius" should be --sanguis--;

Col. 22, line 25, "sangius" should be --sanguis--;

Col. 22, line 27, "sangius" should be --sanguis--;

Col. 22, line 29, "sangius" should be --sanguis--;

Col. 22, line 31, "sangius" should be --sanguis--;

Col. 22, line 34, "sangius" should be --sanguis--;

Col. 22, line 36, "sangius" should be --sanguis--;

Col. 22, line 37, "sangius" should be --sanguis--;

Col. 22, line 38, "sangius" should be --sanguis--.